(12) United States Patent
Hall et al.

(10) Patent No.: US 10,159,228 B2
(45) Date of Patent: Dec. 25, 2018

(54) PRECISION WATER DELIVERY SYSTEM FOR INSECTS

(71) Applicant: Aspire Food Group USA Inc., Austin, TX (US)

(72) Inventors: Michael Todd Hall, Austin, TX (US); Gabriel Mott, Austin, TX (US); Mohammed Ashour, Austin, TX (US)

(73) Assignee: Aspire Food Group USA Inc., Austin, TX (US)

( * ) Notice: Subject to any disclaimer, the term of this patent is extended or adjusted under 35 U.S.C. 154(b) by 0 days.

(21) Appl. No.: 15/202,763

(22) Filed: Jul. 6, 2016

(65) Prior Publication Data

US 2018/0007874 A1 Jan. 11, 2018

(51) Int. Cl.
| | |
|---|---|
| *A01K 67/033* | (2006.01) |
| *A01K 7/02* | (2006.01) |
| *A01K 29/00* | (2006.01) |
| *G05D 7/06* | (2006.01) |

(52) U.S. Cl.
CPC .............. *A01K 67/033* (2013.01); *A01K 7/02* (2013.01); *A01K 29/005* (2013.01); *G05D 7/0635* (2013.01)

(58) Field of Classification Search
CPC ........ A01K 67/033; A01K 7/02; A01K 7/025; A01K 7/04; A01K 29/005; A01K 39/024; A01K 7/00; A01K 31/005; A01K 31/17; A01K 31/18; A01K 31/22; A01M 1/00; A01M 1/02; A01M 1/10; A01M 1/103; A01M 1/106; A01G 27/00; A01G 27/001; A01G 27/003; A01G 27/005; A01G 27/006; A01G 27/008; A01G 27/04; A01G 31/02; A01G 31/06
See application file for complete search history.

(56) References Cited

U.S. PATENT DOCUMENTS

| | | | | |
|---|---|---|---|---|
| 3,375,808 | A | * | 4/1968 | Freeman .............. A01K 67/033 119/496 |
| 3,486,486 | A | | 12/1969 | Vanderborgh, Jr. et al. |
| 3,650,244 | A | | 3/1972 | Fordham |
| 3,745,977 | A | | 7/1973 | Martin |
| 4,010,888 | A | * | 3/1977 | Gilbert ................. B65D 5/4295 119/454 |
| 4,286,546 | A | | 9/1981 | Moore |

(Continued)

FOREIGN PATENT DOCUMENTS

| | | | | |
|---|---|---|---|---|
| JP | WO 2012073948 | * | 6/2012 | .......... A01K 67/033 |
| WO | WO-2005063008 A2 | * | 7/2005 | .......... A01K 67/033 |

(Continued)

OTHER PUBLICATIONS

United States Patent Office Action for U.S. Appl. No. 15/377,394 dated Oct. 31, 2017 (15 pages).

(Continued)

*Primary Examiner* — Kathleen I Alker
(74) *Attorney, Agent, or Firm* — Lee & Hayes, PLLC

(57) ABSTRACT

A water delivery system for supplying water to an insect habitat. The water delivery system including a water tray equipped with a sensor to monitor an amount of water within a water tray. The sensor to cause water to be delivered to the water tray when the amount of water within the tray falls below a predefined threshold amount.

20 Claims, 11 Drawing Sheets

(56) References Cited

U.S. PATENT DOCUMENTS

| | | | |
|---|---|---|---|
| 4,485,763 A | 12/1984 | Icking | |
| 4,498,420 A * | 2/1985 | Botternnan | A01K 67/033 119/6.5 |
| 4,646,687 A | 3/1987 | Peterson et al. | |
| 4,850,305 A * | 7/1989 | Georgi | A01K 67/033 119/303 |
| 4,892,059 A | 1/1990 | Yoneyama | |
| 4,903,636 A | 2/1990 | Kroeker | |
| 5,174,245 A | 12/1992 | Bishop | |
| 5,791,287 A | 8/1998 | Gruber | |
| 5,799,440 A | 9/1998 | Ishikawa et al. | |
| 5,887,544 A | 3/1999 | Popelier | |
| 6,105,535 A * | 8/2000 | Atamian | A01K 67/033 119/246 |
| 6,474,259 B1 * | 11/2002 | Gaugler | A01K 67/033 119/6.7 |
| 6,990,768 B1 * | 1/2006 | Boston | A01M 1/02 119/69.5 |
| 7,229,627 B2 | 6/2007 | Hoffman et al. | |
| 7,555,866 B2 | 7/2009 | Kania et al. | |
| 7,975,649 B2 | 7/2011 | Barker | |
| 8,683,954 B2 | 4/2014 | Page | |
| 8,733,284 B2 * | 5/2014 | Courtright | A01K 29/00 119/6.6 |
| 8,802,919 B2 | 8/2014 | Hoffman et al. | |
| 8,813,684 B2 | 8/2014 | Buchanan | |
| 8,844,465 B2 * | 9/2014 | Holland | A01M 1/106 119/6.5 |
| 2006/0086037 A1 * | 4/2006 | Roberts | A01M 1/02 43/107 |
| 2012/0187041 A1 * | 7/2012 | Popa | A01K 67/033 210/602 |
| 2013/0319334 A1 * | 12/2013 | Newton | A01K 67/033 119/6.5 |
| 2015/0122182 A1 * | 5/2015 | Aldana | A01K 67/033 119/6.6 |
| 2015/0144068 A1 | 5/2015 | Quinta Cortinas | |
| 2015/0208609 A1 * | 7/2015 | Tillet | A01K 7/02 119/74 |
| 2015/0237826 A1 * | 8/2015 | Van Der Poel | A01K 7/02 119/74 |
| 2017/0172083 A1 | 6/2017 | Villamar | |
| 2018/0007874 A1 | 1/2018 | Hall et al. | |

FOREIGN PATENT DOCUMENTS

| | | | | |
|---|---|---|---|---|
| WO | WO 2009058101 | * | 5/2009 | A01M 1/02 |
| WO | WO 2015023178 | * | 2/2015 | A01K 67/033 |
| WO | WO 2015111007 | * | 7/2015 | A01K 67/033 |

OTHER PUBLICATIONS

Office Action for U.S. Appl. No. 15/377,394, dated Mar. 29, 2018, Hall et al., "Precision Water Delivery System for Insects", 13 pages.

Office Action for U.S. Appl. No. 15/377,394, dated Jul. 25, 2018, Hall et al., "Precision Water Delivery System for Insects", 15 pages.

* cited by examiner

PRECISION WATER DELIVERY SYSTEM FOR INSECTS

BACKGROUND

Today most insects that are cultivated for human consumption are housed in single use cardboard boxes, plastic bins or immobile large troughs made of wood or concrete. In insect husbandry, providing water to the insects is usually achieved by manually filling or placing a bottle or similar distribution device within an insect habitat. Unfortunately, recently hatched insects are extremely fragile and easily drowned by surface tension of a single droplet of water. Thus, the water within the bottle may drown a significant number of insects prior to being emptied. Additionally, when bottles are replaced, the insects, particularly with larva or baby insects that are hard to see, may be removed with the bottles decreasing the overall populations and human interaction with the insects may lead to damage, such as crushing or smashing of the insects, or passing of pathogens, filth, or other contaminants between populations. Finally, approaches to mechanical replenishment of watering devices are inadequate due to the inconsistency of filling (water consumption rates tend to vary between bins) and cost (for economic and practical reasons, most establishments of insect husbandry do not have a 24-hour operational cycle and consequently tend to have at least one work shift where watering devices are not replenished).

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
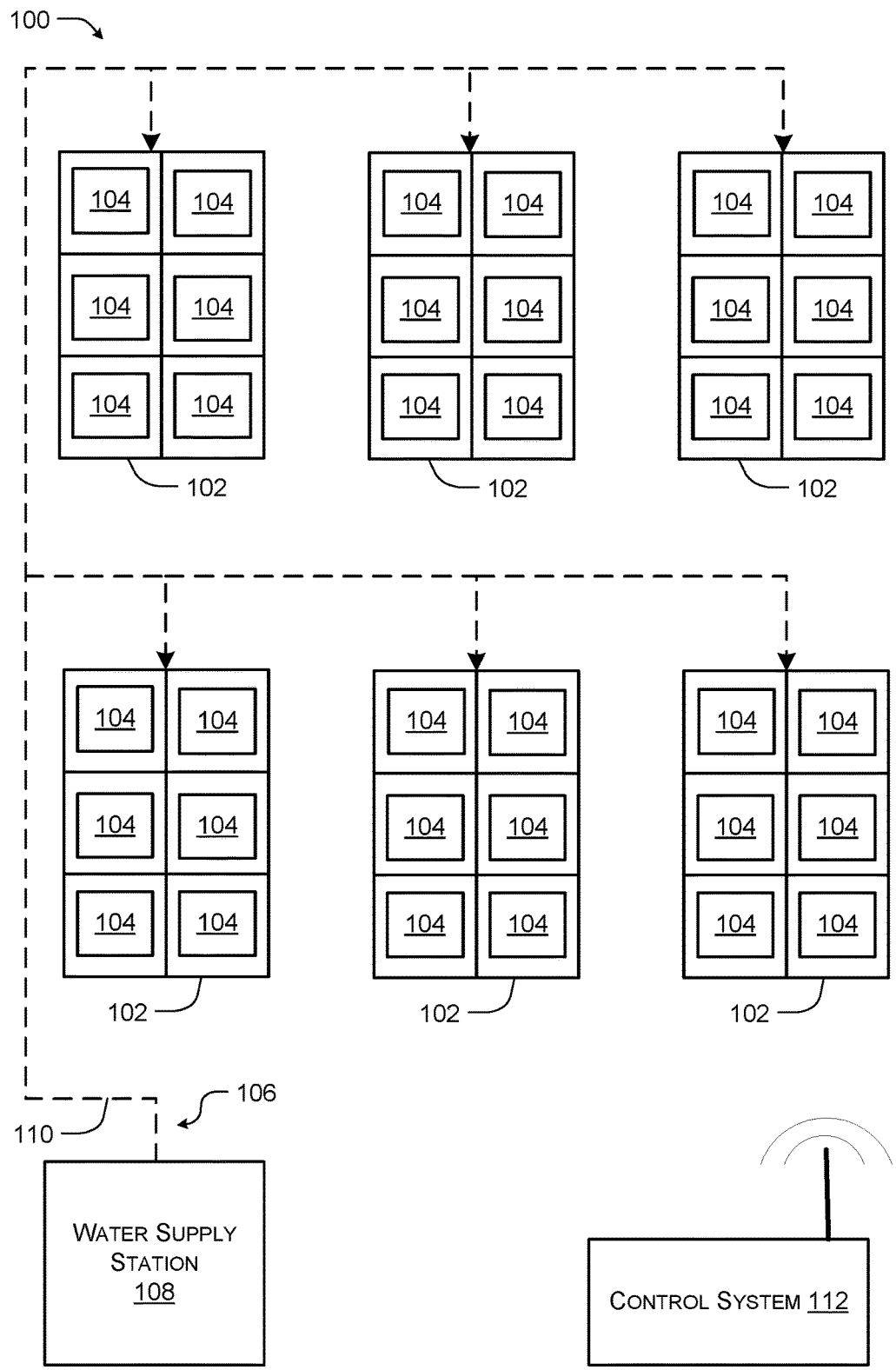
FIG. 1 illustrates an example facility having multiple racks of insect habitats and water delivery system for cultivating insects according to some implementations.

Described herein are implementations and techniques for distributing water to insects. For example, live insects may be cultivated in habitats containing individual populations. Each habitat may include a water tray that the insects within the habitat may access from time to time. Periodically, the water tray should be filled to maintain a consistent water supply for the insect population. Traditionally, a bottle filled with water may be placed by hand within the habitat. Unfortunately, live insects may cling to the bottle as the bottle is removed and insects may be drowned by surface tension of a single droplet of water including the water within the bottle, thereby reducing the population. Additionally, the human interaction with the insects may pass pathogens, filth, or other contaminants from habitat to habitat or crush or smash the insects within the habitats, particularly, during the insects' early developmental stages.

In some implementations described herein, a water delivery system may be configured to deliver a consistent water supply to the insect habitats without requiring human interaction with the habitats. For example, a facility designed for cultivating insects may be outfitted with a rack system configured to hold or house multiple insect habitats in vertical rows to increase the overall output of the facility. In general, the rack system is designed to improve the efficiency of cultivating live insects, such as crickets, grasshoppers, mealworms, and other insects that have a flightless stage, by minimizing the insects' exposure to human interaction and reducing deaths caused by drowning. In some instances, the vertical racks may be placed adjacent to or side-by-side. The racks may also be grouped such that various groups of racks may support habitats that each contain insects in the same stage of development (e.g., each habitat in the group contains eggs, larvae, infants or pin heads, larger immature insects, or adult insects). In another instance, insects may be contained in horizontally or laterally positioned habitats and the water delivery system may be configured to supply water via troughs within the horizontally positioned habitats. In one particular example, the habitats may be long troughs or continuous habitats arranged in rows. In these instances, the water delivery system may be configured to provide water in a manner that supports the particular life stage of the insects within the assigned group of habitats or racks.

In some cases, each habitat may also be designed with a dividing insert or unit. The insert may be included to increase the overall total surface area within the same volume previously contained within the habitat, thereby improving overall yields per-volume. The habitat inserts generally form a grid, helix or cross-section within the interior space of the habitat. In some cases the inserts are designed to be removable from the habitat. Thus the vertical wall design of the inserts may assist with harvesting of the insects when the insert is removed from the habitat. For example, the inserts may be moved over a bin and vibrated to cause the insects to fall off of or detach from the vertical surfaces of the insert.

Additionally, the inserts may be configured to receive a water tray into a depressed region on the top surface of the insert at predetermined locations. The water tray may be configured to receive water from the water delivery system and distribute the water to the insects. The type or configuration of the water tray may vary depending on the life stage of the insects within the habitat. For example, for smaller insects, which are easily drowned, the water tray may include an area having fibrous or porous material, such as peat moss, coconut fiber, etc., that may absorb water on the tray. The insects may access the water within the porous material without the risk of drowning. In other examples, as the insects mature, the insects may be unable to obtain sufficient water from the porous material. In these examples, the water tray may include a perforated float that allows the insects to access the water within the tray without being able to fall into and drown, as the insects are predisposed to do in standing water.

In some instances, the water tray may be configured with various sensors, such as weight sensors, temperature sensors, moisture sensors, float sensors, contact sensors, proximity sensors, water gauges, image components, pH monitors etc., that may collect data related to the amount of water or moisture associated with the water tray. The water tray may also be configured to provide the data and/or signal the water delivery system (or a controller associated therewith) to distribute water to the water tray when the water level, saturation level, or moisture level fall below a corresponding water level threshold, saturation threshold, or moisture threshold. In one particular instance, the water delivery system may distribute water onto the water tray until a second signal is received from the water tray indicating that the water level, saturation level, or moisture level has risen above a second corresponding water level threshold, saturation threshold, or moisture threshold.

In some instances, an image component may be utilized to collect image data usable to detect the presence of any dead or drowned insects within the water tray and to alert a facility operator to the presence of the dead or drowned insects. The image data may also be analyzed to cause an adjustment to an amount of water the water delivery system distributes to the particular habitat experiencing an issue.

In some implementations, described herein, the water delivery system may distribute water to individual habitats or water trays at a rate corresponding to the combined rate at which a population of insects within each of the habitats consumes the water, the rate at which water is lost to evaporation and any other factors that contribute to water loss. Thus, a consistent water level may be maintained within each habitat without exposing the insects to human contact and/or risk of drowning.

FIG. 1 illustrates an example facility 100 having multiple racks 102 of insect habitats 104 and a water delivery system 106 for cultivating insects according to some implementations. In the illustrated example, a water supply station 108 may be configured to distribute water to the habitats 104 along one or more of water delivery tubes, generally indicated by 110. In some cases, the water delivery tubes 110 may include one or more valves or other devices to route or divert water to the habitats 104.

A control system 112 may be directly coupled to the water delivery system 106 and/or the habitats. Alternatively, the control system 112 may be in wireless communication with the water delivery system 106 and/or the habitats 104. The control system 112 may be configured to open and close various valves and shut off devices to deliver water from the water supply station 108 to one or more of the habitats 104 at any particular time.

In some instances, each of the habitats 104 may be configured with sensors and/or image components that collect sensor and image data associated with the corresponding habitat and/or one or more water trays positioned within the corresponding habitat. The sensor and/or image data collected by the habitats 104 may be provided to the control system 112 or processed by the habitats 104 to determine that the corresponding habitat 104 is low on water. For example, a water tray associated with each of the habitats 104 may be configured with various sensors, such as weight sensors, moisture sensors, float sensors, contact sensors, proximity sensors, water gauges, etc., that may collect data related to the amount of water or moisture associated with the water tray. In this instance, the water tray may provide the data and/or signal the control system 112. The control system 112 may analyze the data and cause the water delivery system 106 to distribute water to the tray when the control system 112 the water level, saturation level, or moisture level fall below a corresponding water level threshold, saturation threshold, or moisture threshold. In one particular instance, the water delivery system may distribute water onto the water tray until the control system 112 determines that the water level, saturation level, or moisture level associated with the water tray has risen above a second corresponding water level threshold, saturation threshold, or moisture threshold.

Figure 2:
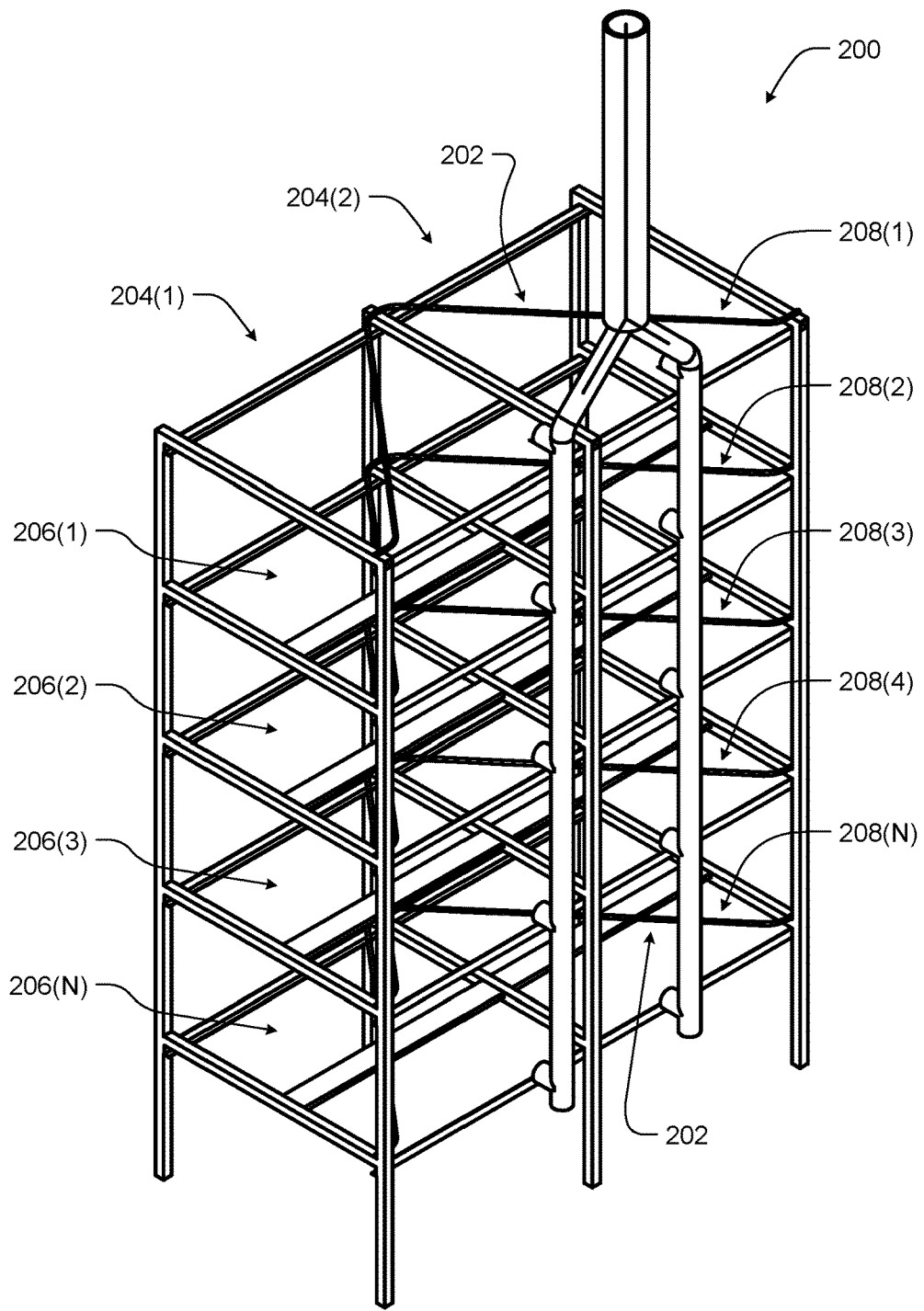
FIG. 2 illustrates an example rack equipped with a water delivery system according to some implementations.

FIG. 2 illustrates an example rack 200 equipped with a water delivery system 202 according to some implementations. In the illustrated example, the rack system configured to hold or house multiple insect habitats in vertical columns, generally indicated by 204(1) and 204(2), to increase the overall output of the facility. In general, the rack 200 is designed to improve the efficiency of cultivating live insects, such as crickets, grasshoppers, mealworms, and other insets that have a flightless stage, by minimizing the insects' exposure to human interaction and reducing deaths caused by drowning. For instances, in the current example, the columns 204(1) and 204(2) are positioned adjacent to or side-by-side each other. The columns 204 may also be grouped such that various groups of racks may support habitats that each contain insects in the same stage of development (e.g., each habitat in the group contains eggs, larvae, infants or pin heads, larger immature insects, or adult insects). In these instances, the water delivery system 202 may be configured to provide water in a manner that supports the particular life stage of the insects within the assigned group of habitats or racks.

In the current example, the adjacent columns of racks 204(1) and 204(2) together with additional columns of racks (not shown) may form multiple rows for housing habitats, generally indicated by 206(1)-206(N). Each row 206(1)-206(N) may include corresponding water delivery tubes 208(1)-208(N). Thus, each of the water delivery tubes 208(1)-(N) may deliver water to the habitats housed within the rows 206(1)-206(N). In some cases, each row of water delivery tubes 208(1)-208(N) may include a corresponding valve to open and close the flow of water through the water delivery tubes 208(1)-208(N), thereby controlling the delivery of water to the habitats housed within the corresponding rows 206(1)-206(N). For example, larva insects may be cultivated within habitats on the row 206(1) and larva insects may consume water at a rate that the water delivery system 202 distributes water to the larva once per day. Similarly, larger immature insects may be cultivated within habitats on the row 206(2) and larger immature insects may consume water at a rate that the water delivery system 202 distributes water to the larva twice per day. Thus, the water delivery tube 208(1) may be opened once a day and the water delivery tube 208(2) may be opened twice a day based on a predetermined schedule.

Figure 3:
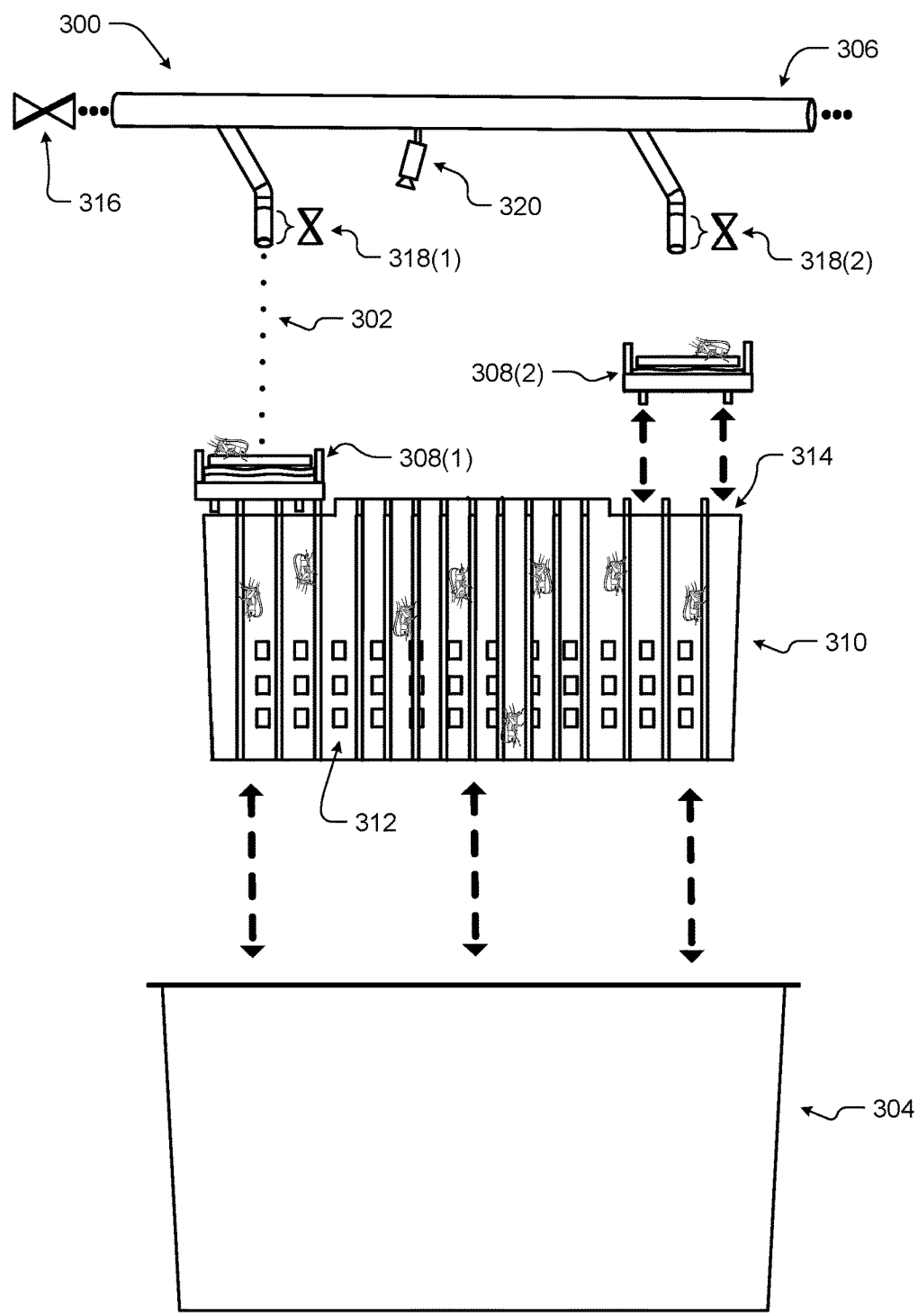
FIG. 3 illustrates an example of a water delivery system distributing water to a habitat according to some implementations.

FIG. 3 illustrates an example of a water delivery system 300 distributing water 302 to a habitat 304 according to some implementations. In the illustrated example, a water delivery tube 306 associated with the water delivery system 300 is distributing the water 302 onto a first water tray 308(1) associated with the habitat 304. The habitat 304 includes a habitat insert 310 currently shown as removed from the habitat 304. The insert 310 may be included in the habitat 304 to increase the overall total surface area within the same volume previously contained within the habitat 304, as the increase in surface area results in a corresponding increase in the insects that may be cultivated within the same volume of space. In the illustrated example, the insert 310 may generally form a grid, helix or cross-section within the interior space of the habitat 304. As shown in the illustrated example, the insert 310 may be removable from the habitat 304 and include vertical walls that allow the insert 310 to be shaken to be dislodged or removed from the habitat 304 during harvesting in a more efficient manner. For example, the insert 310 may be moved over a collection bin and vibrated to cause the insects to fall off of or detach from the surfaces of the insert 310. The insert 310 may also include perforations 312 along the interior walls to increase airflow and insect mobility throughout the entire volume and allow the insects to more easily reach the water tray 308(1).

In the current example, the insert 310 is configured to receive the first water tray 308(1) as well as a second water tray 308(2) shown removed from the insert 310. For instance, the water trays 308(1) and 308(2) may be removable for cleaning prior to or following the harvesting of the insects. In some cases, the water trays 308(1) and 308(2) may be positioned at predetermined locations within the habitat 304, for instance, by including a depressed region 314 on the top surface of the insert 310. Thus, the water trays 308(1) and 308(2) may be easily positioned at a location within the habitat 304 to receive water 302 from the water delivery tube 306. In the illustrated example, two water trays 308(1) and 308(2) are shown. However, it should be understood that the habitat 304 and/or the insert 310 may be configured to hold any number of water trays.

The water delivery tube 306 may be configured to include various valves, such as illustrated water tube valve 316 and/or water tray valves 318(1) and 318(2), for controlling the amount of water 302 and the timing associated with the delivery of the water 302 to each of the water trays 308(1) and 308(2). For instance, the water tube valve 316 may be opened and closed to control the amount of water 302 entering the water delivery tube 306. Likewise, the water tray valves 318(1) and 318(2) may be opened and closed to control the amount of water 302 distributed to the corresponding water tray 308(1) and 308(2). Again, it should be understood that while the illustrated example includes two water tray valves 318(1) and 318(2) any number of water tray valves may be included in the water delivery system 300. For example, the number of water tray valves may correspond to the number of water trays on each habitat.

In some examples, the water trays 308(1) and 308(2) may be configured with various sensors or switches, such as weight sensors, temperature sensors moisture sensors, float sensors, contact sensors, proximity sensors, water gauges, pH monitors, image components, etc., that may collect data related to the amount of water, saturation, or moisture remaining on the water trays 308(1) and 308(2). In some instances, the data collected by the sensors may be provided to the water delivery system 300, a control system (such as control system 112 of FIG. 1), or analyzed by a component or circuit associated with the water trays 308(1) and 308(2) to control the water tube valve 316 and/or the water tray valves 318(1) and 318(2). For instance, in the illustrated example, a sensor associated with the water tray 308(1) may indicate that the water level, saturation level, or moisture level has fallen below a corresponding threshold, while a sensor associated with the water tray 308(2) may indicate that the water level, saturation level, or moisture level has remained above the threshold. Thus, the water delivery system 300 may open the valves 316 and 318(1) to allow the water 302 to fall onto the water tray 308(1) but close the valve 318(2) to prevent the water 302 from falling on the water tray 308(2). In this manner, each water tray 318(1) or 318(2) may receive water 302 on demand and at an amount to prevent pooling of water that may result in the insects in the habitat 304 in drowning.

In some cases, the water 302 distributed by the water delivery tube 306 may be at a rate that is controlled to prevent splashing, disturbing the contents of the water trays and/or the water 302 reaching a velocity at which the water 302 may squash, crush, or otherwise kill the insects within the habitat 304. For example, the water delivery tube 306 may be positioned relatively close to the water trays 308(1) and 308(2), such that the water 302 has little distance to fall prior to impacting the water trays 308(1) or 308(2). In some cases, the amount of water 302 and/or the distance between the water delivery tube 306 and the water trays 308(1) and 308(2) may be selected based on a life stage, type, and/or size of the insects within the habitat 304.

In some implementations, an image device 320 may be positioned to capture image data associated with the water trays 308(1) and/or 308(2). The image data captured by the image device 320 may be processed to determine if one or more insects are present on the water trays 308(1) or 308(2). For example, the water tray valve 318(1) or 318(2) may be closed when insects are present on the corresponding water tray 308(1) or 308(2) to prevent incidental insect death due to the falling water 302. In the illustrated example, a single image device 320 is shown; however, it should be understood that any number of image devices 320 or components may be utilized to monitor the water trays 308(1) and 308(2). For instance, an image device may be associated with each of the water trays associated with the habitat 304. Additionally, in lieu of an image device 320 various sensors may be incorporated into the habitat 304, water trays 308(1) and 308(2), the rack, or the water tube 306. For instance, thermal sensors or weight sensors on the water trays 308(1) and 308(2) may collect data usable to determine the presence of insects. Further, in the current example, the image device 320 is shown as attached to the water tube 306, however, in other implementations the image device 320 may be attached or coupled at other locations associated with the habitat 304, such as the rack, the habitat 304, and the water trays 308(1) and 308(2), among others.

Figure 4:
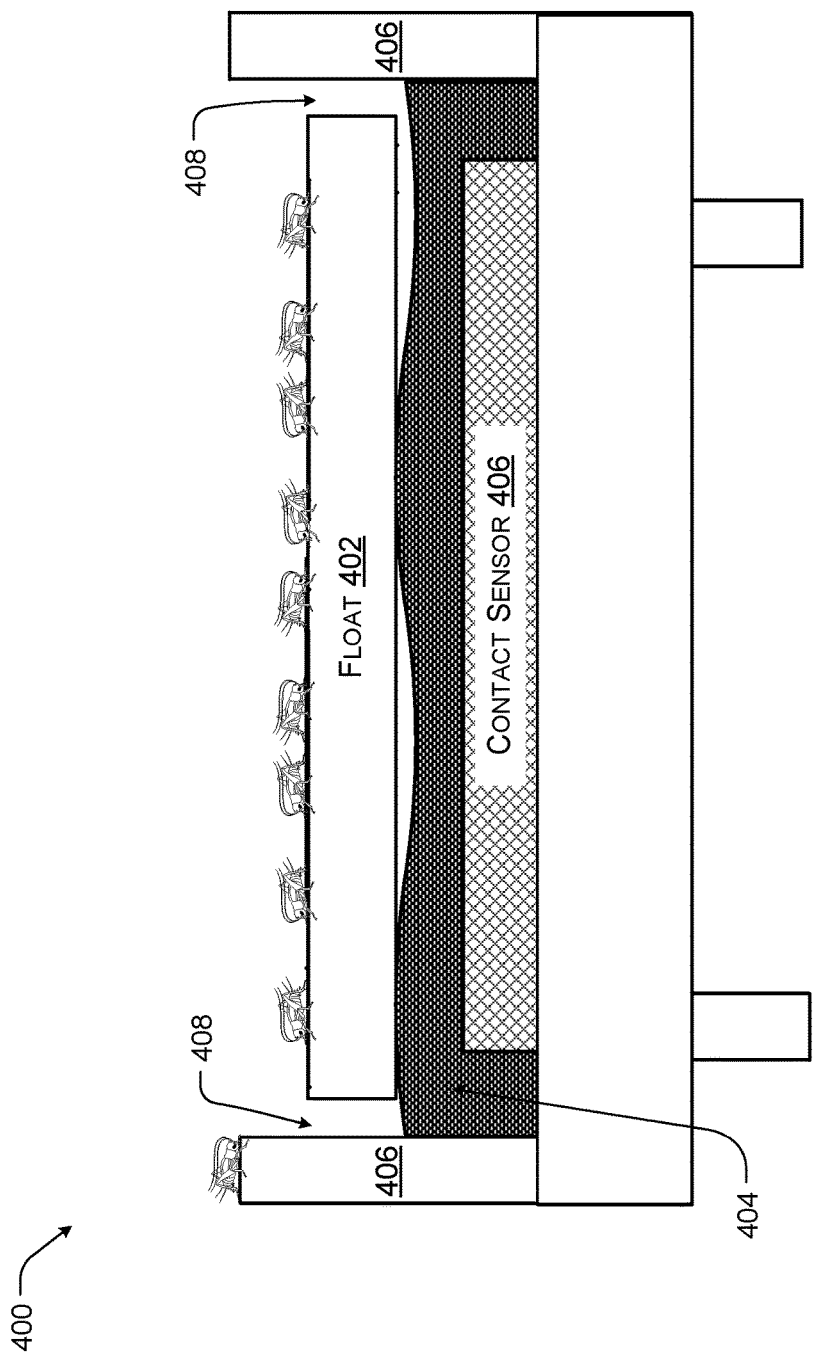
FIG. 4 illustrates an example water tray according to some implementations.

FIG. 4 illustrates an example water tray 400 according to some implementations. The water tray 400 is one example of a water tray 400 designed for adult and larger immature insects for which the risk of self-drowning is reduced. In the illustrated example, the water tray 400 includes a float 402 that is configured to move up and down based on an amount of water 404 located within the tray 400. In some implementations, the float 402 may be separated from the walls 406 of the tray 400 by an air gap, generally indicated by 408. For example, the air gap 408 may allow the float 402 to move up and down on the water 404 more easily. In some cases, the size of the air gap 408 may be based on a size of the insects within the habitat. For example, the total size of the air gap 408 on both sides of the float 402 may be less than a size of the insects within the habitat to prevent the insects from falling into the water and drowning.

In some cases, the float 402 may include perforations that allow the insects to drink or otherwise consume the water 404 through the float 402. The perforations within the float 402 may be sized to prevent the insects from drowning. Thus, as the insects within a habitat increase in size, the floats 402 may be replaced such that the size of the perforations remain consistent with the size and needs of the insects (e.g., large enough to allow the insects to drink but small enough to prevent the insects from being pulled into the water 404).

In the current example, the water tray 400 also includes a contact or pressure sensor 410. For instance, as the insects consume the water 404 the float 402 may move closer and closer to the contact or pressure sensor 410. Eventually as a level of the water 404 falls below a threshold (based on the height of the contract sensor 410), the float 402 impacts the contact sensor 410. The impact between the float 402 and the sensor 410 may cause the sensor 410 to trigger and signal a control system (such as the control system 112 of FIG. 1) or a component associated with the water delivery system. In this example, one or more valves associated with the water delivery system may be opened to allow a predetermined amount of water 404 to be added to or deposited into the water tray 400. The additional water 404 causes the float 402 to rise and removes the contact between the float 402 and the sensor 410.

It should be understood that while the illustrated example shows a contact or pressure sensor 410 various other types of sensors may be utilized to measure the water level or amount of water associated with the tray 400. For example, FIG. 5 below shows an alternate water tray including a water gauge.

Figure 5:
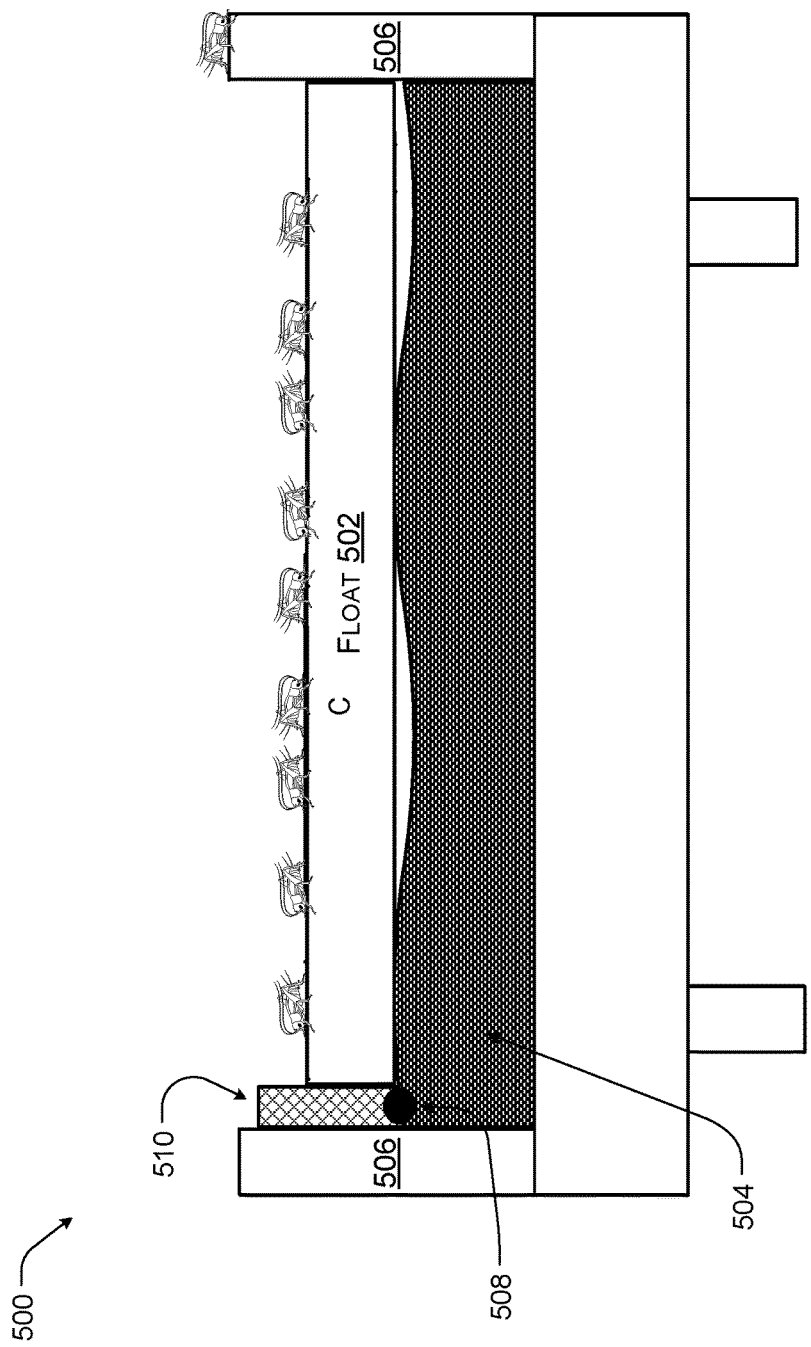
FIG. 5 illustrates an example water tray according to some implementations.

FIG. 5 illustrates an example water tray 500 according to some implementations. Similarly to the water tray 400 of FIG. 4, the water tray 500 is an example of a water tray 500 designed for adult and larger immature insects for which the risk of self-drowning is reduced. In the illustrated example, the water tray 500 includes a float 502 that is configured to move up and down based on an amount of water 504 located within the tray 500. In this implementation, the float 502 may contact the walls 506 of the tray 500 to prevent insects from falling into and drowning in the water 504. For example, the walls 506 may be formed from a material having a low coefficient of friction or coated with a material having a low coefficient of friction to allow the float 502 to move up and down within the tray 500 without scraping or sticking to the side walls 506.

As discussed above, the float 502 may include perforations that allow the insects to drink or otherwise consume the water 504 through the float 502. The perforations within the float 502 may be sized to prevent the insects from drowning. Thus, as the insects within a habitat increase in size, the floats 502 may be replaced such that the size of the perforations remain consistent with the size and needs of the insects (e.g., large enough to allow the insects to drink but small enough to prevent the insects from being pulled into the water 504).

In the current example, the water tray 500 also includes a contact or water gauge sensor 510. For instance, as the insects consume the water 504 a water sensor 508 may measure the level of the water 504 within the tray 500. Eventually as a level of the water 504 falls below a threshold, the sensor 510 may signal a control system (such as the control system 112 of FIG. 1) or a component associated with the water delivery system. In this example, one or more valves associated with the water delivery system may be opened to allow additional water 504 to be added or deposited into the water tray 500. As the additional water 504 fills the tray 500, the sensor 510 may determine the water level has met or exceeded a second threshold (e.g., a full threshold) and signal the control system or component to cause the valves to close.

Figure 6:
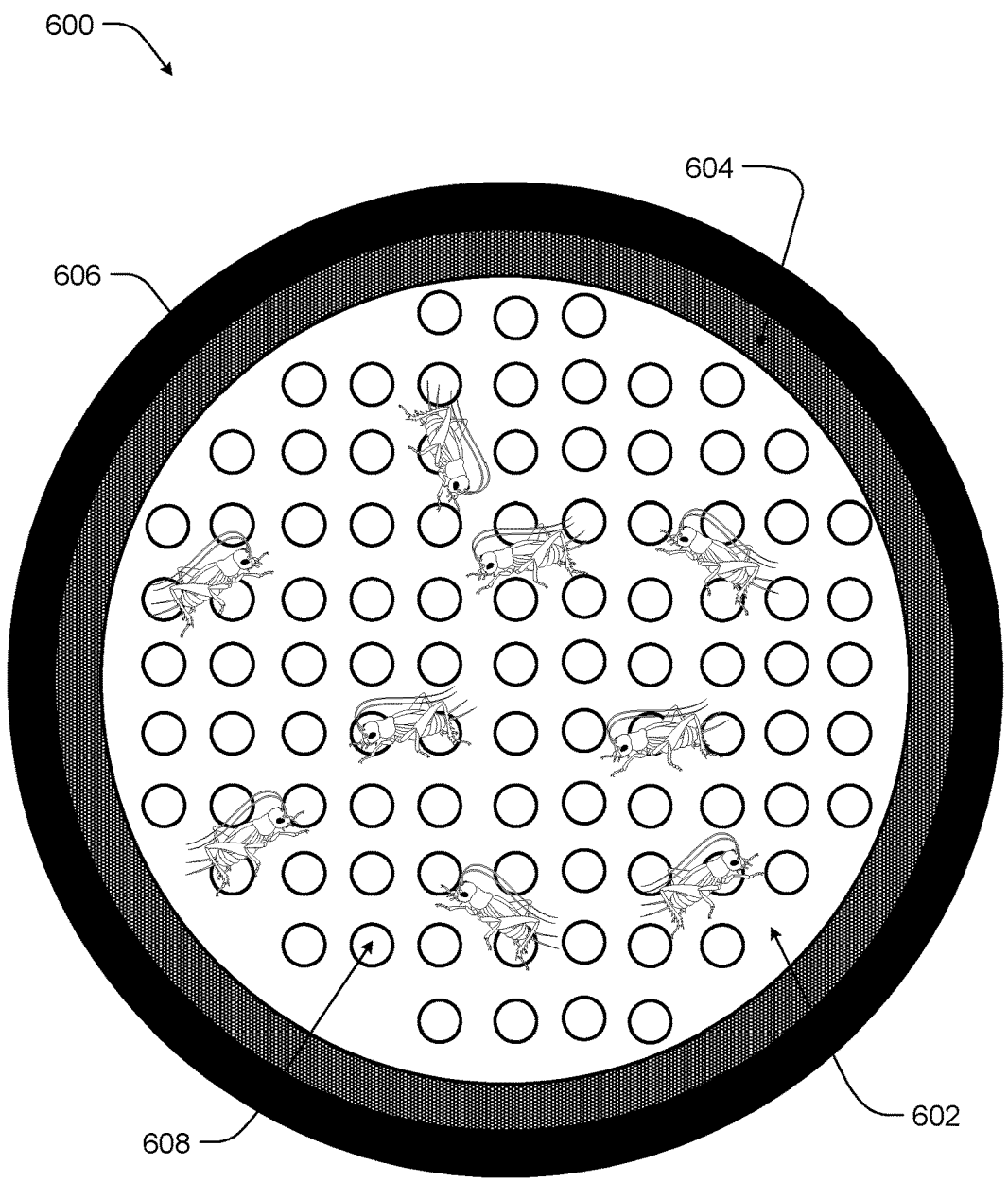
FIG. 6 illustrates a top view of the example water trays of FIGS. 4 and 5 according to some implementations.

FIG. 6 illustrates a top view of the example water trays of FIGS. 4 and 5 according to some implementations. The water tray 600 is an example of a water tray 600 designed for adult and larger immature insects for which the risk of self-drowning is reduced. In the illustrated example, the water tray 600 includes a float 602 that is configured to move with a level of water 604 located within the tray 600. In the illustrated example, the float 602 may include perforations 608 that allow the insects to drink or otherwise consume the water 604 through the float 602. The perforations 608 within the float 602 may be sized to prevent the insects from drowning. Thus, as the insects within a habitat increase in size the floats 602 may be replaced such that the size of the perforations 608 remain consistent with the size and needs of the insects (e.g., large enough to allow the insects to drink but small enough to prevent the insects from being pulled into the water 604).

Figure 7:
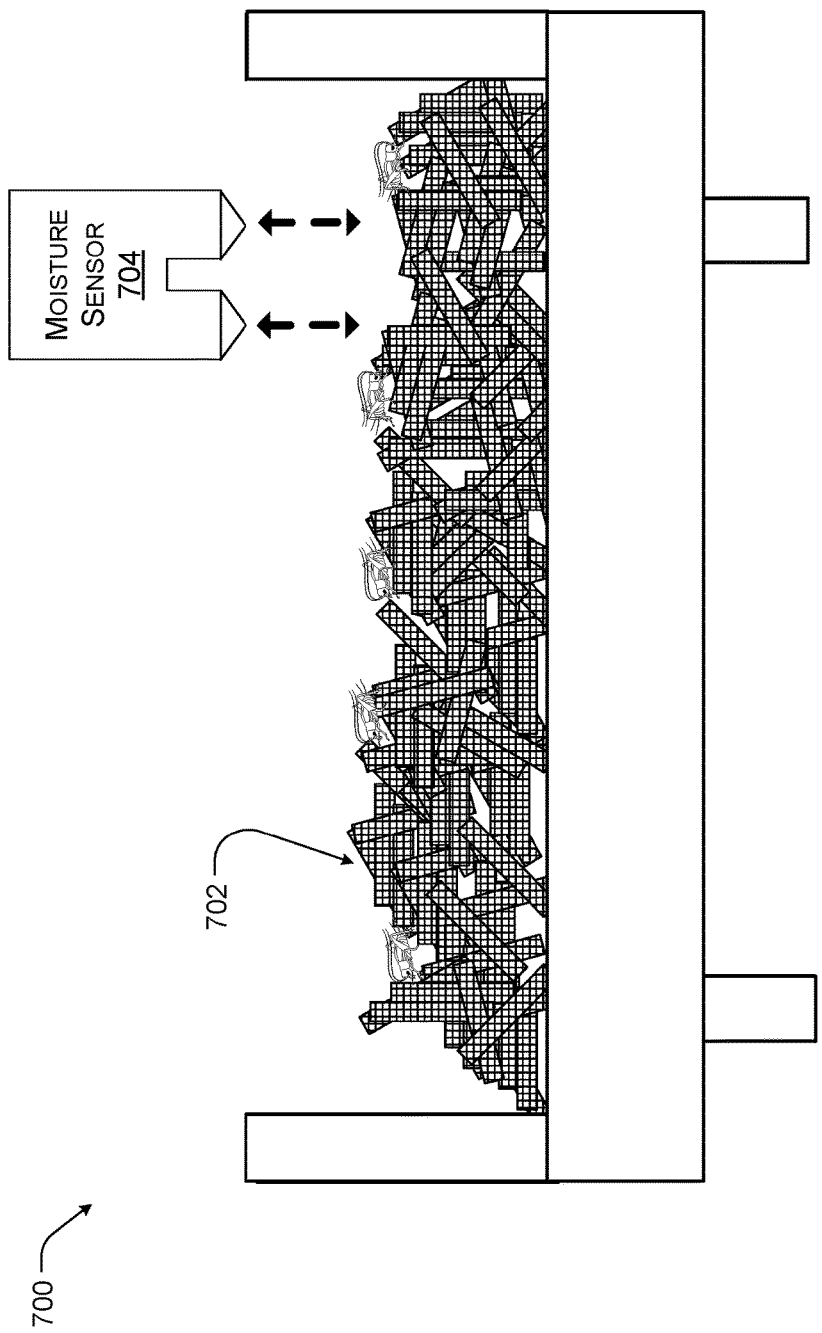
FIG. 7 illustrates an example water tray according to some implementations.

FIG. 7 illustrates an example water tray 700 according to some implementations. The water tray 700 is one example of a water tray 700 designed for newly hatched insects for which the risk of self-drowning is high. In the illustrated example, the water tray 700 includes a plurality of fibrous or porous material 702, such as peat moss or coconut fiber, that may absorb and retain moisture. For example, the insects may be able to suck or otherwise withdraw the moisture from the fibrous material 702 in sufficient amounts to remain viable.

In the current example, the water tray 700 also includes a moisture or saturation sensor 704. For instance, the insects may extract moisture from the porous material 702 eventually causing the porous material 702 to become dry. The moisture or saturation sensor 704 may monitor the level of moisture or saturation associated with the porous material 702 and signal a control system (such as the control system 112 of FIG. 1) or a component associated with the water delivery system when the level of moisture or saturation falls below a corresponding threshold. The water delivery system may cause water to be released and deposited onto the porous material 702 to be absorbed. As the water is absorbed, the moisture or saturation sensor 704 may determine the moisture or saturation level of the porous material 702 meets or exceeds a second threshold and signal the control system or component to cause the water delivery to the water tray 700 to halt.

In the illustrated example, the moisture or saturation sensor 704 is shown as removed. However, in other examples, the moisture or saturation sensor 704 may be connected, attached, or otherwise coupled to the water tray 700.

Figure 8:
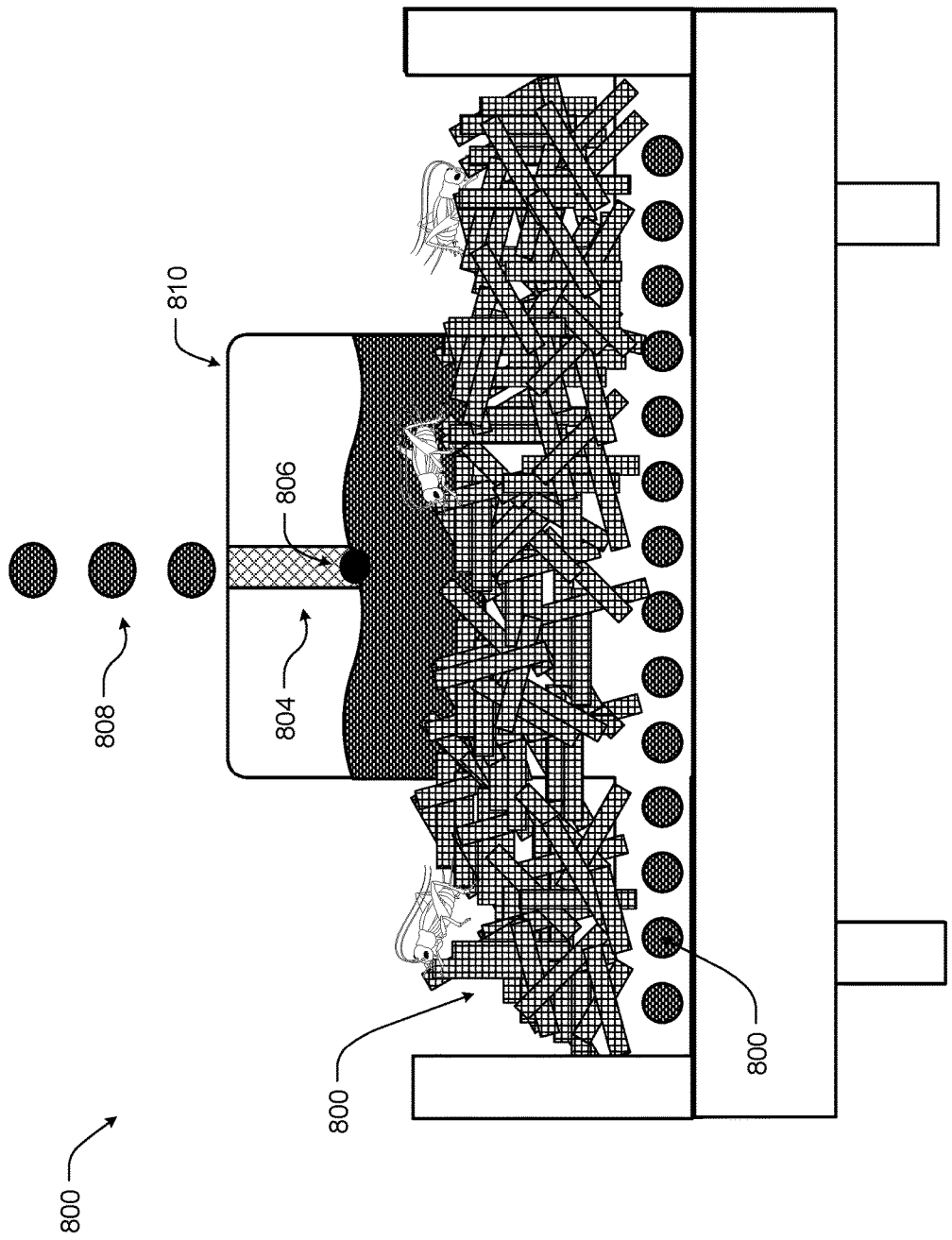
FIG. 8 illustrates another example water tray according to some implementations.

FIG. 8 illustrates an example water tray 800 according to some implementations. The water tray 800 is another example of a water tray 800 designed for newly hatched insects for which the risk of self-drowning is high. In the illustrated example, the water tray 800 includes a plurality of fibrous or porous material 802, such as peat moss or coconut fiber, that may absorb and retain moisture. For example, the insects may be able to suck or otherwise withdraw the moisture from the fibrous material 802 in sufficient amounts to remain viable.

In the current example, the water tray 800 also includes a water gauge sensor 804 having a float 806 that measures an amount of water 808 within a water retention area 810. The water retention area 810 may be positioned to receive the water 80 released from the water delivery system (not shown). The walls of the water retention area 810 may be of sufficient height and/or have a coefficient of friction below a threshold to prevent the insects from entering the water retention area 810 via the opening at the top. The bottom of the water retention area 810 may include a number of perforations 812 that allow the water 808 to be absorbed by the porous material 802. In some cases, the perforations 812 may be sized to prevent the insects from burrowing through the porous material and into the water retention area 810, thereby preventing the insects from drowning.

In an example, the insects may extract moisture form the porous material 802 eventually causing the water level in the water retention area 810 to fall below a threshold. The water gauge sensor 804 may signal a control system (such as the control system 112 of FIG. 1) or a component associated with the water delivery system when the threshold is met or exceeded. The water delivery system may cause water to be released and deposited into the water retention area 810 via the opening in the top, as shown. As the water fills the water retention area 810, the water gauge sensor 804 may determine that the water level meets or exceeds a second threshold and signal the control system or component to cause the water delivery to the water tray 800 to halt.

Figure 9:
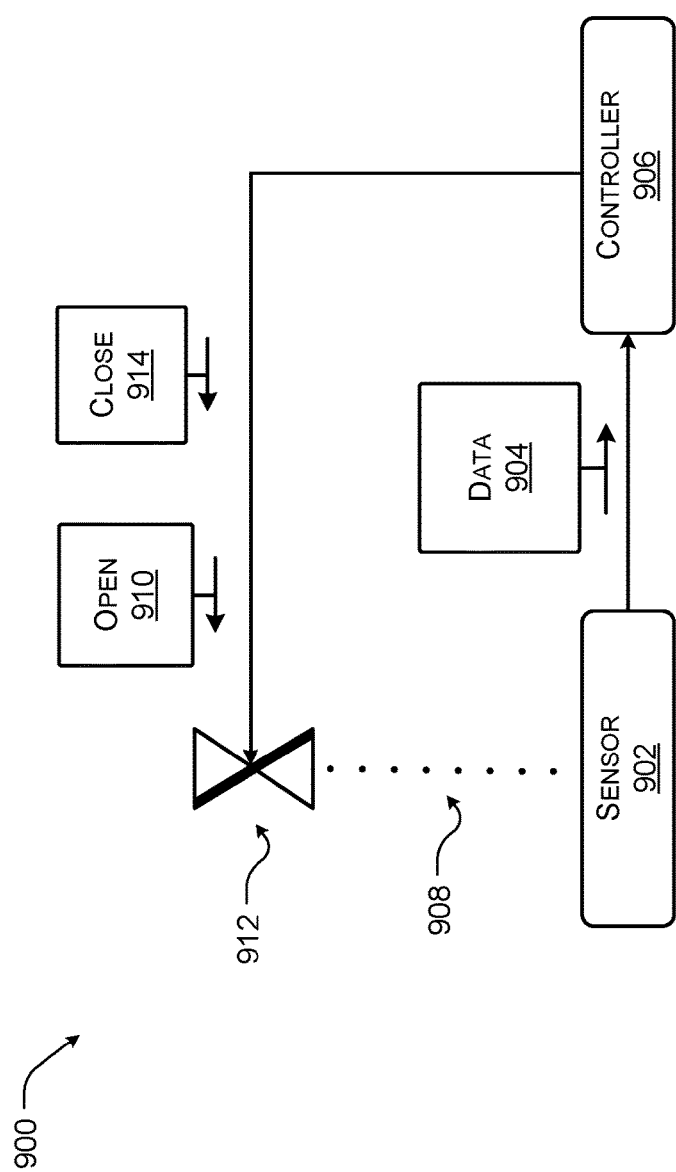
FIG. 9 illustrates an example circuit for controlling water delivery to an insect habitat according to some implementations.

FIG. 9 illustrates an example circuit 900 for controlling water delivery to an insect habitat according to some implementations. In the illustrated example, a sensor 902 may collect data 904 related to water levels, moisture levels, and consumption rates associated with the insect habitat. The sensor may include one or more weight sensors, moisture sensors, float sensors, contact sensors, proximity sensors, water gauges, image components, etc., that may collect data related to the amount of water or moisture present in a water tray.

The data 904 may be provided to a controller 906 via a wired or wireless communication channel. In some cases, the controller 906 may analyze or process the data 904 to determine an amount of water 908 to deliver to the habitat. In some cases, the data 904 may be provided at regular intervals and the amount of water 908 to be added to the habitat may be determined by the controller 906 at each interval. In other cases, the sensor 902 may send the data 904 in response to the water level or moisture level falling below a minimum water level threshold or the controller 906 may determine from the data 904 that the water level or moisture level is below the minimum water level threshold. In these cases, the controller 906 may send a first signal 910 or open signal to a valve 912 associated with the habitat. The open signal 910 may cause the valve to open and deliver the water 908 to the habitat. The sensor 902 may then send the data 904 in response to the water level or moisture level exceeding a maximum or full water level threshold or the controller 906 may determine from the data 904 that the water level or moisture level has exceeded the maximum or full water level threshold. In these cases, the controller 906 may send a second signal or close signal 914 to a valve 912 associated with the habitat. The close signal 914 may cause the valve to close and halt the delivery of the water 908 to the habitat.

Figure 10:
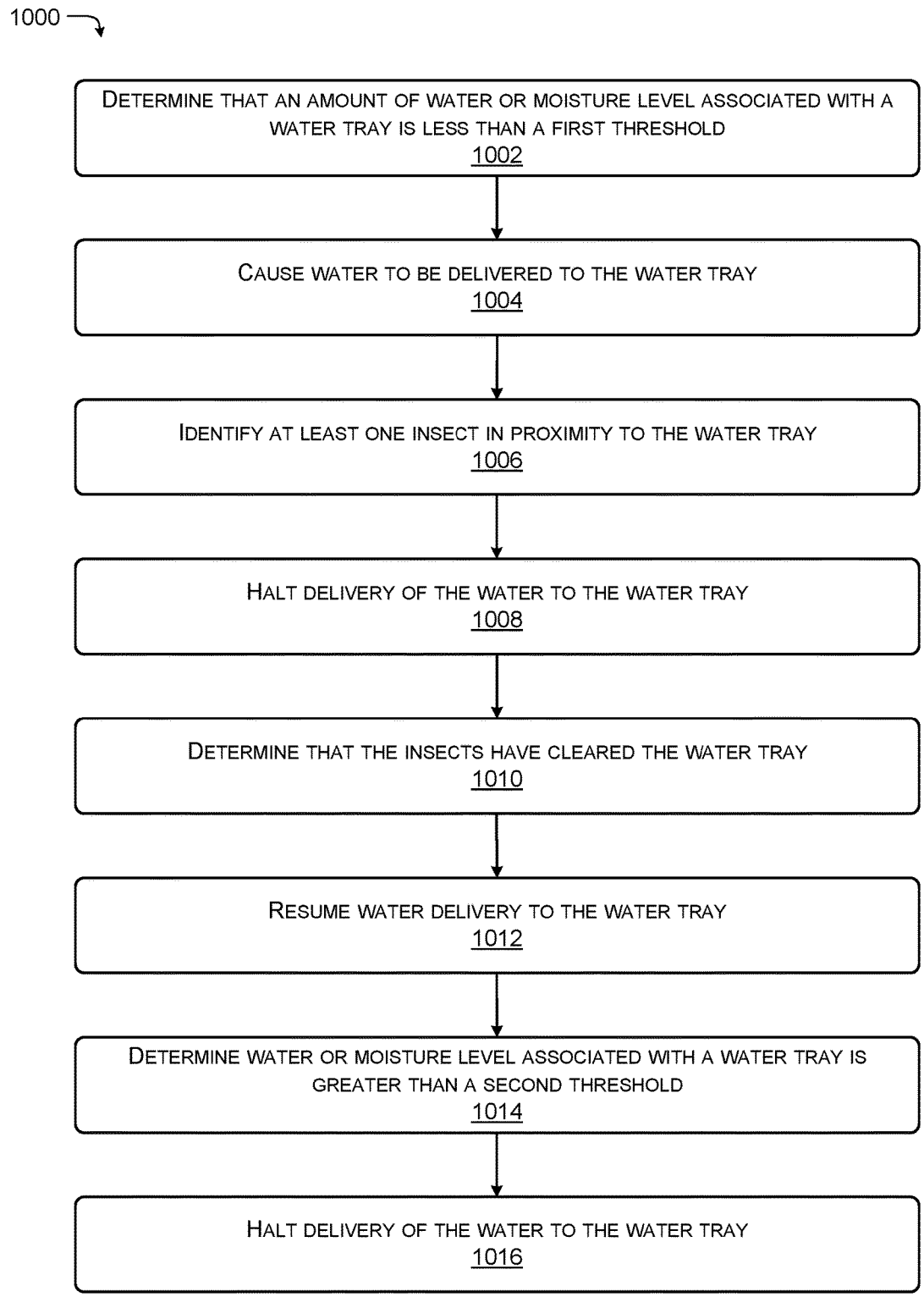
FIG. 10 illustrates an example flow diagram showing an illustrative process associated with the water delivery system according to some implementations.

FIG. 10 provides an example flow diagram illustrating an example process for implementing the water delivery systems described above. The process is illustrated as a collection of blocks in a logical flow diagram, which represent a sequence of operations, some or all of which can be implemented in hardware, software or a combination thereof. In the context of software, the blocks represent computer-executable instructions stored on one or more computer-readable media that, when executed by one or more processors, perform the recited operations. Generally, computer-executable instructions include routines, programs, objects, components, data structures and the like that perform particular functions or implement particular abstract data types.

The order in which the operations are described should not be construed as a limitation. Any number of the described blocks can be combined in any order and/or in parallel to implement the process, or alternative processes, and not all of the blocks need be executed. For discussion purposes, the processes herein are described with reference to the frameworks, architectures and environments described in the examples herein, although the processes may be implemented in a wide variety of other frameworks, architectures or environments.

FIG. 10 illustrates an example flow diagram showing an illustrative process associated with the water delivery system according to some implementations. As described above, a water delivery system may be configured to deliver a consistent water supply to the insect habitats without requiring human interaction with the habitats. For example, a facility designed for cultivating insects may be outfitted with a rack system configured to hold or house multiple insect habitats in vertical rows to increase the overall output of the facility. In general, the rack system is designed to improve the efficiency of cultivating live insects, such as crickets, grasshoppers, mealworms, and other insets that have a flightless stage, by minimizing the insects' exposure to human interaction and reducing deaths caused by drowning.

At 1002, the water delivery system determines that an amount of water or moisture level associated with a water tray is less than a first threshold. In some cases, the water tray may be equipped with one or more sensors to monitor the water level and/or moisture level. For example, the sensor may include weight sensors, moisture sensors, float sensors, contact sensors, proximity sensors, water gauges, image components, etc.

At 1004, the water delivery system cause water to be delivered to the water tray. For example, a controller may cause one or more valves to allow water to be dispensed onto the tray at a predetermined rate. In some cases, the valves may include a room valve, a rack valve, a row and/or column valve, a habitat valve, and/or a water tray valve. In particular example, the valves may control an amount of water and/or a rate of water delivery based upon an opening setting. For example, the valve may have a variable opening size that allows the water to be dispensed at a high rate when the opening size is increased. In other examples, the valve associated with the water tray may include various nozzle setting, such as spray, shower, trickle, drip, among others.

At 1006, the water delivery system may identify at least one insect in proximity to the water tray. For example, the water delivery system, the water tray, and/or the habitat may include an image device or component that may capture information associated with the habitat and/or the insects within the habitat. In some cases, the water delivery system may be configured to dispense water onto the tray when the insects are a predetermined distance from the tray or the area at which the water lands on the tray. The image data collected by the image device or component may be analyzed by, for example, a controller to determine the presence of the insects and to control the timing associated with the water delivery. In other cases, the water tray or habitat may be equipped with various sensors, such as thermal sensors or weight sensors that may track the position of the insects within the tray or habitat.

At 1008, the water delivery system may halt the delivery of water to the water tray. For example, when the image data indicates that an insect is present on or proximate to the water tray or an area at which the water is received at the water tray, the controller may cause one or more of the valves to close. Thus, the water delivery system may prevent injury or death of insects due to water delivery by monitoring the location of the insects within the habitat. In other examples, the controller may reduce the water delivery rate or the nozzle type associated with the delivery to prevent the injury or death of other insects.

At 1010, the water delivery system may determine that the insects have cleared the tray or moved out of proximity with the tray. For example, the controller may analyze or process the image data and determine that the insect in proximity has moved on. In other cases, data collected by one or more sensor, such as a thermal sensor, may indicate the insect has moved on.

At 1012, the water delivery system may resume water delivery. For example, the controller may then cause one or more valves to again allow water to be dispensed onto the tray at the predetermined rate.

At 1014, the water delivery system determines that an amount of water or moisture level associated with a water tray is greater than a second threshold. As discussed above, the water tray may be equipped with one or more sensors to monitor the water level and/or moisture level. For example, the sensor may include weight sensors, moisture sensors, float sensors, contact sensors, proximity sensors, water gauges, image components, etc.

At 1016, the water delivery system may halt the delivery of water to the water tray. For example, when the second threshold is met or exceeded, the water tray may be full or unable to accommodate additional water. Thus, the controller may cause one or more of the valves to close to prevent the water tray from overflowing and, thereby, drowning insects within the habitat.

Figure 11:
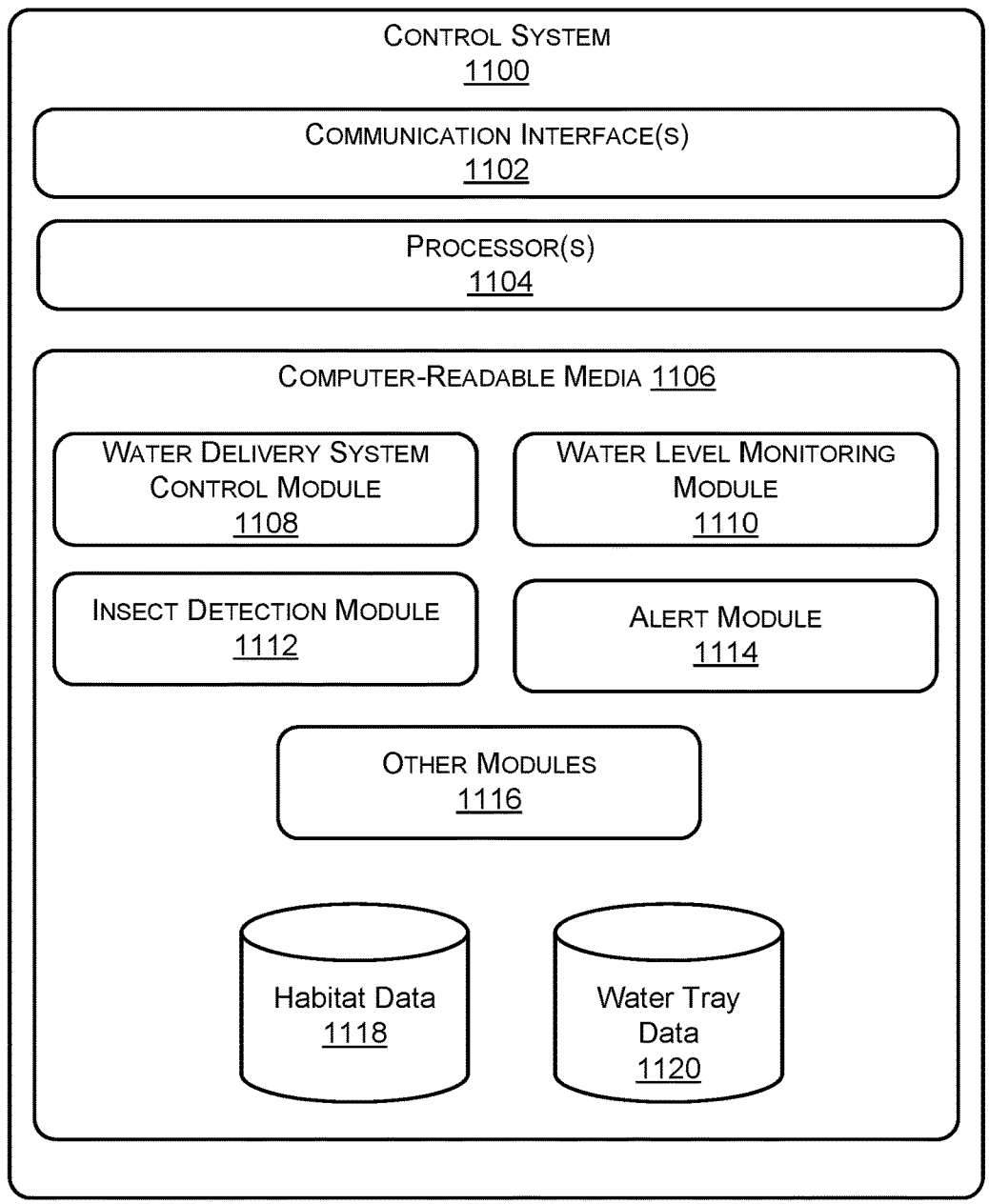
FIG. 11 illustrates example components of a control system 1100 associated with a water delivery system according to some implementations.

FIG. 11 illustrates example components of a control system 1100 associated with a water delivery system according to some implementations. For example, the control system 1100 may be configured to process image and/or sensor data collected by a water tray, habitat, rack, water delivery system, and/or facility to control the flow of water to individual water trays on a tray by tray basis.

In the illustrated example, the control system 1100 includes one or more communication interfaces 1102. The communication interfaces 1102 are configured to facilitate communication between one or more networks and/or other devices, such as water control valves, sensors and image devices associated with the facility, habitat, or water tray, and/or other devices associated with the facility. In some cases, the communication interfaces 1102 may also facilitate communication between one or more wireless access points, a master device, and/or one or more other computing devices as part of an ad-hoc or local network systems. The communication interfaces 1102 may support both wired and wireless connection to various networks, such as cellular networks, radio, Wi-Fi networks, short-range or near-field networks (e.g., Bluetooth®), infrared signals, local area networks, wide area networks, the Internet, and so forth.

The control system 1100 may also include one or more processors 1104, such as at least one or more access components, control logic circuits, central processing units, or processors, as well as one or more computer-readable media 1106 to perform the functions associated with the control system 1100. Additionally, each of the processors 1104 may comprise of one or more processors or processing cores.

Depending on the configuration, the computer-readable media 1106 may be an example of tangible non-transitory computer storage media and may include volatile and non-volatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 1104.

Several modules such as instructions, data stores, and so forth may be stored within the computer-readable media 1106 and configured to execute on the processors 1104. For example, as illustrated, the computer-readable media 1106 stores a water delivery system control module 1108, a water level monitoring module 1110, insect detection module 1112, an alert module 1114, as well as other modules 1116. The computer-readable media 1106 may also be configured to store data, such as habitat data 1118 collected and received from the habitats within the facility and water tray data 1120 related to a state of each individual water tray in the facility.

The water delivery system control module 1108 may be configured to control one or more valves associated with a water delivery system. By opening and closing values, as well as adjusting nozzle size and type, the water delivery system control module 1108 may be able to control the timing, rate, and distribution of water or moisture onto each individual feed tray in near real time.

The water level monitoring module 1110 may receive data related to the amount of water in each individual water tray and process the data to determine if the water delivery system control module 1108 should cause water to be dispensed to a particular water tray. For example, the water level monitoring module 1110 may analyze the data to determine if the water or moisture associated with a water tray is below a minimum threshold or above a maximum threshold.

The insect detection module 1112 may analyze data received from the habitats and/or water tray to determine issues associated with the water tray. For example, if an insect is in a hazard area and has risk of injury or death if water is dispensed, the insect detection module 1112 may notify the water delivery system control module 1108. In other examples, if dead insects or other debris is detected within the water tray, the insect detection module 1112 may notify the alert module 1114.

The alert module 1114 may be configured to determine if an issue associated with the habitat or water tray. For example, if the insect detection module 1112 identifies one or more dead insects on the water tray, the alert module 1114 may cause a notation or alert to be provided to a facility operator to check on the particular habitat. In another example, if the water level monitoring module 1110 determines the water level is above a spill threshold, than the alert module 1114 may notify the operator that the habitat corresponding to the water tray is experiencing an issue and/or that the water delivery system may be malfunctioning.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A system for distributing water to an insect having a high risk of self-drowning, the system comprising:

an insert positioned within an insect habitat, the insert comprising at least one vertical wall that has perforations;

a water tray positioned within the insect habitat and configured to couple with the insert, the water tray configured to provide moisture to the insect, the water tray including at least one wall that at least partially defines a water retention area, the water retention area configured to receive the moisture from a water delivery tube via a first opening of the water tray, and the water retention area configured to prevent the insect from self-drowning;

a sensor to collect data related to a level of the moisture associated with the water retention area; and a water delivery system configured to:
 receive the data from the sensor;
 determine that a minimum moisture threshold has been met based at least in part on the data; and
 in response to determining that the minimum moisture threshold has been met, cause the moisture to be provided to the water tray via the first opening of the water tray.

2. The system as recited in claim 1, wherein the water tray includes a porous material to absorb the moisture, a top surface of the porous material is configured to be above the level of the moisture, the top surface of the porous material extending over the length and width of the water retention area, and a bottom surface of the porous material includes a number of perforations that allow the moisture to be absorbed by the porous material.

3. The system as recited claim 2, wherein the porous material is coconut fiber.

4. The system as recited in claim 2, wherein the number of perforations are sized to prevent the insect from burrowing through the porous material.

5. The system as recited in claim 1, wherein the sensor is at least one of:
 a moisture sensor;
 temperature sensor;
 pH monitor;
 a contact or pressure sensor positioned on a base of the water tray;
 a contact or pressure sensor positioned on a float of the water tray;
 a weight sensor;
 a proximity sensor positioned on the base of the water tray; or
 a water gauge.

6. The system as recited in claim 5, wherein a state of the water tray is associated with a location and a health of the insect.

7. The system as recited in claim 1, further comprising an image device, configured to collect data associated with a state of the water tray.

8. A system for distributing water to an insect having a high risk of self-drowning, the system comprising:
 a water delivery tube configured to distribute the water to an insect habitat, the water delivery tube having:
  a first valve to control water flow to the insect habitat;
  a control circuit to open and close the first valve; and
  an insert positioned within the insect habitat, the insert comprising at least one vertical wall that has perforations;
 a water tray within the insect habitat and positioned below the water delivery tube, the water tray having:
  a platform configured to mate with the insert, the platform including at least one wall to form an area, the area to receive the water distributed from the water delivery tube;
  a sensor associated with the platform to collect data associated with an amount of water within the area, the sensor to provide the data to the control circuit via a communication channel between the sensor and the control circuit; and
 wherein the control circuit causes the first valve to open and close based at least in part on the data collected by the sensor.

9. The system as recited in claim 8, wherein the water delivery tube includes:
 a second valve to control the water flow to a rack associated with the insect habitat; and
 a third valve to control the water flow to a room associated with the rack.

10. The system as recited in claim 8, wherein the at least one wall is at least one of the following: a wall of a receptacle or an exterior wall of the water tray.

11. The system as recited in claim 10, wherein:
 the at least one wall is the wall of the receptacle; and
 the receptacle is positioned to receive the water from the water delivery tube and disperse the water into a plurality of fibrous material.

12. The system as recited in claim 8, wherein the water tray includes a plurality of fibrous material and a number of perforations, wherein the number of perforations are sized to prevent the insect from burrowing through the plurality of fibrous material.

13. The system as recited in claim 8, wherein the water tray includes a plurality of fibrous material that absorbs additional moisture received in response to the opening of the first valve.

14. The system as recited in claim 8, wherein the water tray includes at least one of the following:
 a plurality of fibrous material, wherein the plurality of fibrous material is at least one of peat moss, coconut fiber, rocks, pebbles, perforated plastic rings, or plastic balls, plastic objects; or
 a float.

15. The system as recited in claim 8, wherein the sensor is at least one of:
 a moisture sensor;
 a contact or pressure sensor positioned on a top surface of a base of the water tray; a contact or pressure sensor positioned on a bottom surface of a float of the water tray;
 a weight sensor;
 a proximity sensor positioned on a top surface of the base of the water tray; or
 a water gauge.

16. The system as recited in claim 8, further comprising:
 a second valve to control water flow to the insect habitat;
 a second water tray positioned below the water delivery tube, the second water tray having:
  a second platform configured to mate with the insert, the platform including at least one wall to form a second area, the second area to receive second water distributed from the water delivery tube to the second water tray;
  a second sensor associated with the second platform to collect second data associated with a second amount of water within the second area, the second sensor to provide the second data to the control circuit via a second communication channel between the second sensor and the control circuit; and wherein the control circuit causes the second valve to open and close based at least in part on the second data collected by the second sensor.

17. The water tray system as recited in claim 16, wherein:

the control circuit causes the first valve to open when the first data indicates the first amount of water in the first tray is below a first threshold and causes the second valve to open when the second data indicates the second amount of water in the second tray is below a second threshold; and the first threshold is the same as the second threshold.

18. The water tray system as recited in claim 16, wherein:

the control circuit causes the first valve to open when the first data indicates the first amount of water in the first tray is below a first threshold and causes the second valve to open when the second data indicates the second amount of water in the second tray is below a second threshold; and the first threshold differs from the second threshold.

19. A water tray system comprising:

an insert positioned within an insect habitat, the insert comprising at least one vertical wall that has perforations;

a first water tray accessible to a first insect, the first water tray configured to couple with the insert, and the first water tray including a first sensor to collect first data associated with a first amount of moisture remaining on the first water tray;

a second water tray accessible to a second insect, the second water tray configured to couple with the insert, and the second water tray including a second sensor to collect second data associated with a second amount of moisture remaining on the second water tray; and a control circuit to:

determine that the first amount of moisture is less than a first threshold;

cause a first amount of water to be delivered to the first water tray based at least in part on the first amount of moisture;

determine that the second amount of moisture is less than a second threshold; and cause a second amount of water to be delivered to the second water tray based at least in part on the second amount of moisture, the second amount of moisture different than the first amount of moisture.

20. The water tray system as recited in claim 19, wherein the control circuit is configured to:

receive, from the first water tray, third data associated with a third amount of moisture remaining on the first water tray;

determine that the third amount of moisture is greater than a third threshold; and halt delivery of the first amount of water to the first water tray based at least in part on the third amount of moisture.

* * * * *